(12) United States Patent
Garrison et al.

(10) Patent No.: US 7,276,553 B2
(45) Date of Patent: Oct. 2, 2007

(54) AESTHETIC, STABLE CHROMATIC EMULSIONS

(75) Inventors: Mark S. Garrison, Suffern, NY (US); Walter J. Carmody, Port Jervis, NY (US)

(73) Assignee: Avon Products, Inc., New York, NY (US)

( * ) Notice: Subject to any disclaimer, the term of this patent is extended or adjusted under 35 U.S.C. 154(b) by 122 days.

(21) Appl. No.: 11/010,097

(22) Filed: Dec. 10, 2004

(65) Prior Publication Data

US 2006/0128883 A1    Jun. 15, 2006

(51) Int. Cl.
*C08L 83/04* (2006.01)

(52) U.S. Cl. ...................... 524/588; 556/444

(58) Field of Classification Search ............. 524/588; 556/444

See application file for complete search history.

(56) References Cited

U.S. PATENT DOCUMENTS

| | | | |
|---|---|---|---|
| 5,162,378 A * | 11/1992 | Guthauser | .............. 514/785 |
| 5,216,033 A | 6/1993 | Pereira et al. | |
| 5,290,555 A * | 3/1994 | Guthauser et al. | .......... 424/401 |
| 5,456,906 A | 10/1995 | Powell et al. | |
| 6,007,799 A | 12/1999 | Lee et al. | |
| 6,086,860 A * | 7/2000 | Brewster | ............... 424/65 |
| 6,379,682 B1 | 4/2002 | Tchinnis et al. | |
| 6,468,512 B1 | 10/2002 | Carmody | |
| 6,685,952 B1 * | 2/2004 | Ma et al. | ............... 424/401 |
| 2003/0190295 A1 | 10/2003 | Fukui et al. | |
| 2004/0081633 A1 | 4/2004 | Mercier et al. | |

OTHER PUBLICATIONS

Chromatic Emulsions, Harry N. Holmes and Don H. Cameron, J. Am. Chem. Soc, v. 44, pp. 71-74 (1922).
Structural Colors in Emulsions, Alfred W. Francis, A.J. Phys. Chem., v. 56, pp. 510-513 (1952).

* cited by examiner

*Primary Examiner*—Kuo-Liang Peng
(74) *Attorney, Agent, or Firm*—Charles J. Zeller; John M. McGillycuddy; Anthony M. Santini

(57) ABSTRACT

A stable, chromatic water-in-silicone emulsion comprising:
i) an aqueous phase containing a water-soluble polyol, a water-soluble polymer thickener, and water; and
ii) a silicone phase containing an aromatic silicone, a silicone emulsifier and a silicone fluid carrier.

33 Claims, No Drawings

AESTHETIC, STABLE CHROMATIC EMULSIONS

SUMMARY OF THE INVENTION

Stable, aesthetic chromatic, water-in-silicone emulsions containing a water soluble polymer in the internal or water phase.

STATE OF THE ART

Chromatic emulsions are emulsions which appear colored due to the refractive effects of the internal and external phases. They are often referred to as having "structural color", since the color seen is not due to any dye or pigment. U.S. Pat. No. 5,290,555 gives the following explanation for this effect. "When two transparent, immiscible liquids are mixed, the combination is often cloudy. If, however, the liquids have the same refractive index (generally measured at 589 nm, i.e., the sodium D line, and 20° C., viz. "$n_D^{20}$"), the mixture will be substantially transparent to the human eye and appear to be homogenous. The appearance of "structural color" in such a mixture requires, not only that the refractive indexes (at a given wavelength of visible light) are the same, but that the variation of the indexes as a function of visible wavelength differ for the two liquids. That is, the "dispersive power" of the two phases must be different".

The chromatic emulsions currently known to the art only able to generate structural color with high levels of non-aesthetic ingredients. In addition, known compositions that exhibit structural color are of the so-called "shake well" type where the effect is easy to generate by shaking but is unstable, i.e. where the internal phase droplets coalesce over time and the color disappears.

Clear emulsions are known in the art but are not the same as chromatic emulsions. For example, U.S. Pat. No. 6,468,512 describes clear water-in-silicone-emulsions prepared by matching refractive index. Such compositions are antiperspirant compositions containing large amounts of aluminum salts.

Chromatic emulsions, also referred to as emulsions exhibiting structural color, are described in JACS, v. 44, pp 71-74 (1922), and A, J. Phys. Chem, v. 56, pp. 510-513 (1952). Although necessarily clear or transparent, chromatic emulsions do exhibit some degree of translucency, and have a rainbow multicolored appearance. Known as curiosities, they have yet to achieve widespread acceptance. Drawbacks such as grossly unacceptable aesthetics and formula instability have remained enormous obstacles.

U.S. Pat. No. 5,290,555 assigned to Revlon describes cosmetic compositions exhibiting structural color, i.e. chromatic emulsions. The compositions contain high levels of polyethylene glycol, higher than 50% in some cases, high levels of oils, such as mineral oil or olive oil, and high levels of emulsifiers. Such compositions would leave a heavy unacceptable feeling on the skin. Lacking stabilizers/clay/waxes, etc. it is likewise obvious the compositions would be of the "shake well" variety and hence, unstable.

Pending application US 2003 190,295 A1 describes color developing compositions. The compositions take advantage of the refractive index of spherical silica to generate color and improve aesthetics. However, none of the examples of the invention as cosmetic preparations are emulsions, or contain water, indicating the applicability of this approach to stabilized aesthetic chromatic emulsions is severely limited and generally unsuitable for cosmetic utilities.

Pending application US 2004 0081 633A1 describes oil-in-water transparent emulsions utilizing sucrose esters. Some of the formulations may exhibit structural color. However, the aesthetics of these oil-in-water systems is poor. Water in silicone systems are not taught; hence, neither the aesthetics nor stability of water-in-silicone systems are addressed at all. The striking lack of commercial products exhibiting structural color speaks to the severe limitations in the art regarding aesthetics and stability of such formations. There is thus a need in the art for stable, aesthetic chromatic emulsions.

OBJECTS OF THE INVENTION

It is an object of the invention to provide stable chromatic water-in-silicone emulsions containing a water-soluble polymer in the internal phase having a light, silky feeling.

It is another object of the invention to provide a novel process for the preparation of the said emulsions.

These and other objects and advantages of the invention will become obvious from the following detailed description.

THE INVENTION

The chromatic water-in-silicone emulsions of the invention are comprised of (1) an aqueous phase containing a water-soluble polyol, a water-soluble polymer thickener and water, and (2) a silicone phase containing an aromatic silicone, a silicone emulsifier and a silicone fluid carrier.

Aspects of the invention that achieve the effects of enhanced stability and aesthetics are the use of a water-in-silicone vehicle, the use of low levels of emulsifiers and oils, the use of an aromatic silicone to generate the structural color, and the addition of a water-soluble polymer to stabilize internal phase droplets. This multi-pronged approach results in a composition that generates structural color having especially light feeling tactile aesthetics and minimal droplet coalescence over time.

Surprisingly, the compositions are stable without the salts usually required in water-in-silicone emulsions. In fact, addition of such salts can destabilize these emulsions, and there inclusion is to be avoided.

In another aspect of the invention, there is the minimal use of emulsifiers. Emulisfiers as a class are designed to emulsify, but in general, are not designed to be aesthetic to the touch. Thus, their over-use can have an adverse effect on the product aesthetics.

A third aspect of the invention is the low use level of the aromatic silicone ingredient. It is believed that the aromatic silicone is critical to the generation of the structural color in the compositions of the present invention, as its refractive index varies with wavelength of visible light while the aqueous phase refractive index remains constant as a function of wavelength. This difference in the refractive index-wavelength relationship between the aqueous phase and the nonaqueous phase has been referred to as the difference in dispersive power between the phase, and while the structural color effect is due to the difference in the dispersive power of the two phases of the composition over the visible spectrum, ingredients of the prior art compositions which gave to rise to this effect result in poor aesthetics, as these ingredients are quite oily or heavy feeling. Non-aesthetic ingredients are ingredients that exhibit poor tactile properties, for example, tackiness, greasiness and inability to be readily absorbed by the skin. Examples of these ingredients are propylene glycol, petrolatum, mineral oil, and the like.

Incorporation of the aromatic silicone permits these ingredients to be incorporated in low levels, or excluded altogether. By use of a low level of the aromatic silicone, the structural color is still obtained, but the result is that aesthetics are markedly improved. The non-aesthetic ingredients may be included in the compositions of the present invention at low levels, generally less than 5% and preferably less than 1% by weight of the emulsion. Most preferably the non-aesthetic ingredients are not present in the composition.

The emulsions of the present invention contain low levels of cyclomethicone. As cyclomethicone is miscible with both alcohol and dimethicone, it can lead to destabilization of water-in-silicone emulsions where alcohol is present in the aqueous phase. The use of alcohol in the aqueous phase of the invention serves to help clarity and improve aesthetics, and also helps to preserve the formulation against microbial growth.

A further aspect of the invention is the use of a hydrophilic polymer in the aqueous internal phase of the composition. By use of such suitable polymer, stability is greatly enhanced, and the need for emulsifiers is further reduced, leading to a more aesthetic composition. Additionally, the polymer serves to thicken the emulsion of the present invention.

It is worth noting that the use of stabilizing salts such as NaCl or MgSO4 is not needed in these emulsions, but is typically required with conventional water-in-silicone emulsions to achieve emulsion stability. In fact, the use of such salts is to be avoided as it will destabilize these compositions. Thus, the combinations of the invention generally contain less than 0.1% salt, preferably less than 0.05% salt, and most preferably none at all.

The compositions of the invention are particularly stable. A common industry protocol for assessing stability consists of filling a 4 oz glass jar with product and placing the jar at 110° F. for a period of 4 weeks. Typically, pH, viscosity, color, odor and texture are evaluated at the beginning and end of the 4 weeks. Further, the sample is examined visually for any liquid separation or syneresis. A stable viscosity profile and a lack of syneresis are particularly important stability parameters. A product is considered stable when there is less than a 25% change in viscosity at 77° F. after stability at 110° F. for four weeks, preferably less than a 10% change, and the sample does not phase separate during the test.

Viscosity measurements were taken using a Brookfield RVF viscometer, using the heliopath stand and TB spindle at 4 RPM. Readings are taken throughout the sample and the average value reported. Viscosity values after 4 weeks are compared to the viscosity when the batch was produced, read at 24 hours.

The water in silicone emulsions of the invention have proven surprisingly stable. Example 1 (below) when tested according to the above criteria showed no syneresis and a superior viscosity profile. This is particularly desirable in a water-in-silicone emulsion, as they often show viscosity declines on stability or even just at ambient storage. To achieve such stability in the absence of inorganic salt, and in the presence of a large amount of alcohol is very remarkable.

| Condition | Viscosity after 4 weeks |
| --- | --- |
| 40 | 26,000 |
| Room Temperature | 25,500 |
| 110° | 25,000 |
| Freeze Thaw test | 26,000 |

These very small differences in viscosity demonstrate exceptional rheological stability. The compositions are also unique in that they give exceptionally clean fragrance rendition, and have exceptionally pleasant aesthetics, and are extremely cost effective.

The compositions of the invention show superior aesthetic properties. One aesthetic parameter which is extremely important is referred to as "tack". It is related to the adhesive and cohesive properties of a composition. Basically, it is how "sticky" a formula is. Tack can be measured instrumentally. The instrument consists of rollers in contact with one another, the product being applied to these rollers. The torque on the top roller is monitored using the computer interface and the more tack the formula has (i.e. the stickier it is), the more torque will be felt on the roller. Thus, tack can be measured in units of force or torque. When measured using the Kershaw Tackmaster-92 with computer interface, available from Kershaw Instrumentation, Inc., the compositions of the invention are surprisingly very low in tack. With instrument settings of 400 RPM, constant temperature bath set to 90 deg F., and sample application amount of 1.3 ml, they show less than 1.5 gm-meters of tack, preferably below 1.0 gm-meters. Readings are taken for at least 1 minute, preferably at least 3 minutes.

Preferably, the aromatic silicone is phenylated and examples of such silicones are phenyl trimethicone, diphenyl dimethicone, trimethyl pentaphenyl trisiloxane, tetramethyl tetraphenyl trisiloxane, phenylpropyl trimethicone, aminopropylphenyl trimethicone, bis phenylhexylmethicone, bis phenylpropyldimethicone, diphenyl isopropyl dimethicone, diphenyl siloxy phenyltrimethicone, phenethyl dimethicone, phenyl dimethicone, phenyl methicone, triphenyl trimethicone, bis diphenylethyl disiloxane, diphenylethyl benzyloxy disiloxane, isopentyl trimethoxycinnamate trisiloxane, phenyl ethyl disiloxane, benzylidene malonate polysiloxane and phenylpropyl ethyl methicone, most preferred is diphenyl dimethicone.

Suitable silicone fluid carriers are a volatile linear or volatile branched silicones, preferably having a viscosity of about 5 centistokes or less, more preferably 2 centistokes or less. Examples of linear silicones are trisiloxane, dimethicone and mixtures thereof, and preferably a blend of trisiloxane and dimethicone with a viscosity of 1.45 to 1.75 centistokes sold under the tradename Dow Corning 2-1184 Fluid An example of volatile branched silicones is methyl trimethicone.

The chromatic water-in-silicone emulsion may contain 0.01-99% by weight, more preferably 0.1 to 50% by weight and most preferably 0.5 to 10% by weight, of silicone fluid carrier, weight being based on the emulsion.

The compositions may also contain a silicone emulsifier such as ethoxylated and/or proepoxylated silicones, with or without alkylation, generally referred to in the art as dimethicone copolyols. Examples of said emulsifiers are, PEG/PPG 19/19 dimethicone, PEG/PPG 18/18 dimethicone, lauryl PEG/PPG 18/18 methicone and cetyl PEG/PPG 10/1 dimethicone. The emulsifier is about 0.1 to 50%, preferably about 1 to 10% by weight of the silicone phase comprising the silicone emulsifier, the aromatic silicone and the silicone carrier, and preferably with the silicone fluid carrier in a greater concentration than the silicone emulsifier.

The water-soluble polyol is a molecule with 3 or more carbon atoms, preferably 3 to 6 carbon atoms, and two or more hydroxyl groups. Examples of suitable polyols are propylene glycol, methyl propanediol, butylene glycol, pentylene glycol, hexylene glycol, glycerin, sorbitol, dipropylene glycol, diglycerine and mixtures thereof. The polyol may be present in an amount of 1 to 90%, more preferably 5 to 50% and most preferably 20 to 40%, by weight of the emulsion.

The chromatic water-in-silicone emulsion may also contain in the aqueous phase, ethanol and/or isopropanol, present in an amount up to about 50%, preferably about 10 to 30% of the aqueous phase.

Examples of the water-soluble polymer thickeners are those containing acrylate monomers, acrylamide monomers or carbohydrate monomers or mixtures thereof. The polymer thickener may be a carbomer polymer such as Carbopol 940. The thickeners may be present in an amount of 0.01% to 5%, more preferably 0.1 to 5%, in particular 0.1 to 3%, and most preferably 0.1 to 1% by weight of the emulsion. Preferred carbomers are those that have reduced impurities, which will provide superior clarity of the emulsion. These preferred carbomers are Carbopol 940, Carbopol 941, Carbopol 980, Carbopol 981, Carbopol Ultrez 10 and Carbopol ETD 2050 and mixtures thereof, all being sold by Noveon.

The refractive index of the aqueous phase is within about 0.0004, preferably about 0.0001, of the refractive index of the silicone phase, to maximize clarity of the final product. This refractive index is measured for convenience for the formulator at the wavelength of sodium 589 nm at 20° C. also known as the D line of sodium using a conventional refractometer such as an ABBE 3L manufactured by Bausch & Lomb. The refractive indexes for each of the phases obtained in accordance with the present invention are generally between 1.3300-1.5900, preferably between 1.3600-1.4900, more preferably between 1.3800-1.4500, more preferably between 1.3900-1.4200 and most preferably between 1.4000-1.4100.

The said refractive indices of the two phases should be sufficiently matched to produce a turbidity of less than 100 NTU at 25° C., more preferably less than 25 NTU and most preferably less than 10 NTU. Turbidity is easily measured using a turbidometer, also known as a nephelometer and is known to those skilled in the art.

The aqueous phase may be 1 to 95%, preferably 50 to 95%, more preferably about 75 to 95%, and most preferably 80 to 90% by weight of the emulsion and the aqueous phase is in the form of droplets with a mean cross-sectional diameter of about 0.1 to 200 microns, preferably 20 to 100 microns.

The compositions of the invention may also comprise at least one member of the group of colorants (dyes, lakes and pigments), fragrances, chelators, UV absorbers, (both UVA and UVB), sunscreens, inorganic sunscreens, particulates, silicone polymeric thickeners, vitamins, antioxidants, botanicals, esters, emollients, humectants, anti-aging ingredients, and pH adjusters in either the aqueous phase or silicone phase depending upon their solubility.

The compositions of the invention as a result of matching the refractive indices of the various phases, are quite clear. Clarity is usually expressed as NTUs, nephelometric turbidity units, and can be easily measured directly using an instrument known as a turbidimeter, such as the Hach 21200 turbidimeter. Turbidity standards can also be obtained and a relative measurement obtained. Standards are readily available from Fisher Scientific and other scientific suppliers, in values ranging from 0.1 to 1000 NTUs.

An estimate of the turbidity can be performed without use of the instrument, simply by visually comparing product samples to the various turbidity standards. This estimation was done in the following manner. Turbidity standards consisting of aqueous solutions of formazine, of 10 NTU and 100 NTU were obtained from the Hach company. By dilution of the 100 NTU standard, reference solutions of 25, 50 and 75 NTU were prepared (for example, dilution of a 100 NTU standard with 50% water yields a 50 NTU solution). Clear round glass vials of 20 ml capacity, are filled with each standard and with the samples to be evaluated. Various typed lowercase characters are typed and printed on a white paper in straight lines, and the paper is placed behind the vials. The text is then viewed looking through the vials. Tests are performed at 25° C. on a 45° angled surface. It is quite easy to arrange the vials in order of clarity. Using standards of, for example, 10 NTU, 25 NTU, 50 NTU, 75 NTU, and 100 NTU and comparing them to the product sample, one can quickly and easily determine where the sample lies in turbidity, just by visual inspection. When tested according to this method, it was determined that the samples of the invention are all clearer than the 100 NTU standard. That is, they have a turbidity significantly less than 100 NTU. Many were less than 25 NTU.

The process for preparing a stable, chromatic water-in-silicone emulsion of the invention comprises:

(a) preparing an aqueous phase containing a water-soluble polyol, a water-soluble polymer thickener and water;

(b) gelling or allowing the aqueous phase to gel;

(c) preparing a silicone phase containing an aromatic silicone, a silicone emulsifier and silicone fluid carrier, and (d) combining the aqueous and silicone phases under sufficient conditions whereby the gel inverts to form a water-in-silicone emulsion with a silicone external phase and an aqueous internal phase.

In the following examples, there are described several preferred embodiments to illustrate the invention. However, it is to be understood that the invention is not intended to be limited to the specific embodiments.

EXAMPLE 1

A stable chromatic emulsion composition of the following components was prepared as follows:

| Phase A (gel phase) | |
|---|---|
| Alcohol (SD40) | 23.00 |
| Water | qs to 100 |
| Glycerin | 23.50 |
| Propylene Glycol | 20.00 |
| Carbopol 940[1] | 1.00 |
| Triethanolamine | 0.88 |
| Phase B (the silicone phase) | |
| Diphenyl dimethicone | 0.75 |
| Dimethicone/trisiloxane blend[2] | 6.75 |
| Dow Corning BY 25-337[3] | 0.5 |

[1]Carbomer, 100% active.
[2]Dow Corning 2-1184 Fluid
[3]PEG/PPG-19/19 dimethicone (50% blend in isoparaffin)

First, the alcohol and water were combined and the Carbopol was dispersed therein with a high shear mixing blade. After 60 minutes, the propylene glycol and glycerin were added to the mixture and mixing was continued for another hour to obtain a smooth dispersion. The mixture was then gelled by addition of triethanolamine mixed with a small amount of glycerin (previously withheld) using an angled prop at a medium speed to avoid incorporating air into the product to instantly form a gel. Upon gelation, the phase goes from hazy fluid to a clear gel. Mixing was continued for another 15 minutes and the refractive indices of the top and bottom of the gel were determined to ensure the gel was uniform, i.e. within 0.0002 of each other.

The last three ingredients were blended together and stirred for about 30 minutes while covered to obtain a clear phase. This silicone phase was slowly added to the Carbopol gel with a prop mixer with slow mixing to avoid splashing. Mixing was then gradually increased so the batch slowly turned over. After 2-3 minutes, the gel inverts and now has a silicone external phase and a gelled aqueous internal phase. The batch was then milled for 5 to 10 minutes at a moderate speed in a Greerco homogenizer to reduce the particle size of the internal phase to about 20 to 70 microns to obtain the chromatic product. If desired, additional components such as fragrances, chelators, UV absorbers, active ingredients, etc., can be added provided they completely dissolve in the aqueous internal phase or the silicone external phase (to avoid turbidity, which is undesirable). If water soluble, they must be added to the aqueous phase before the emulsification step. If they will dissolve in the silicone phase, they may be added at any time.

EXAMPLE 2

In the event air is introduced during the milling step, it can be removed by standing for a day or two or by pulling a vacuum on the sample to remove the air. If the product does not contain air yet, it is hazy when viewed in a glass jar, the refractive index of the two phases was not properly matched to within 0.0004 units, or possibly an ingredient added to one phase, has partitioned somewhat between the two phases. Fragrances or emulsifiers can exhibit this behavior. In such cases, a simple remedial is as follows: Fill 50 grams of the batch into each of 3 glass jars. Add diphenyl dimethicone dropwise to the first jar using the second jar as a control, while adding the dimethicone/trisiloxane blend dropwise to the third. After the addition of each drop, the sample is stirred with a small spatula for 30 seconds. After addition of 2 to 3 drops, one of the two samples should become clearer indicating how the adjustment of the batch should be made. When evaluated according to the turbidity method described earlier, and when a turbidity of 100 NTU or less, preferably 25 NTU or less is achieved, the amount of silicone added to the 50 gram sample is calculated and the batch is then adjusted proportionately.

EXAMPLE 3

Using the procedure of Example 1, a stable chromatic emulsion was prepared from the following components

| Demineralized water | qs |
|---|---|
| Glycerin | 23.40 |
| Propylene Glycol | 20.00 |
| Alcohol SD40 | 22.00 |
| Fragrance | 0.50 |
| Carbopol 940 | 1.00 |
| Triethanolamine | 0.88 |
| Diphenyl Dimethicone | 1.05 |
| Dow Corning 2-1184 Fluid | 7.42 |
| Dow Corning TS 50 IP Fluid[1] | 0.53 |

[1]PEG/PPG-19/19 dimethicone and isoparaffin blend

EXAMPLE 4

Using the procedure of Example 1, the following components were admixed to obtain a chromatic emulsion:

| Demineralized water | qs |
|---|---|
| Phosphoric acid | 0.01 |
| Glycerin | 23.00 |
| Propylene Glycol | 20.00 |
| Alcohol (SD40) | 23.00 |
| Fragrance | 0.50 |
| Carbopol 940 | 1.00 |
| Triethanolamine | 0.88 |
| Diphenyl dimethicone | 0.80 |
| Dow Corning 2-1184 Fluid (dimethicone and trisiloxane mixture) | 6.75 |
| Dow Corning BY25-337[1] | 0.50 |

[1]PEG/PPG-19/19 dimethicone and isoparaffin blend

EXAMPLE 5

Using the procedure of Example 1, the following components were admixed to obtain a chromatic emulsion:

| Demineralized water | qs |
|---|---|
| Glycerin | 23.50 |
| Propylene Glycol | 20.00 |
| Alcohol (SD40) | 23.00 |
| Fragrance | 0.50 |
| Carbopol 940 | 1.00 |
| Triethanolamine | 0.88 |
| Phenylpropylethyl methicone | 1.15 |
| Dow Corning 2-1184 Fluid | 6.35 |
| Dow Corning BY 25-337 Fluid | 0.50 |

Various modifications of the emulsions and method of the invention may be made without departing from the spirit or scope thereof and it is to be understood that the invention is intended only to be limited as defined in the appended claims.

We claim:

1. A stable, chromatic water-in-silicone emulsion comprising:
   i) an aqueous phase comprising from about 1 to about 95% by weight of the emulsion; said aqueous phase comprising:
      (a) one or more water-soluble polyols, said one or more water-soluble polyols comprising from about 20 to about 90% by weight of the emulsion;
      (b) a water-soluble polymer thickener selected from the group consisting of polymers with backbone chains comprising acrylate monomers, acrylamide monomers, carbohydrate monomers, alone or in combination; and
      (c) water; and
   ii) a silicone phase comprising:
      (a) an aromatic silicone, said aromatic silicone comprising from about 0.01% to about 50% by weight of the emulsion;

(b) a silicone emulsifier; and
(c) a silicone fluid carrier;
wherein the refractive index of said aqueous phase is within about 0.0004 of the refractive index of said silicone phase to produce a turbidity of less than or equal to about 100 NTU at 25° C.

2. The chromatic water-in silicone emulsion of claim 1, wherein the aromatic silicone is a phenylated silicone selected from the group consisting of phenyl trimethicone, diphenyl dimethicone, trimethyl pentaphenyl trisiloxane, tetramethyl tetraphenyl trisiloxane, phenylpropyl trimethicone, aminopropylphenyl trimethicone, bis phenylhexylmethicone, bis phenylpropyldimethicone, diphenyl isopropyl dimethicone, diphenyl siloxy phenyltrimethicone, phenethyl dimethicone, phenyl dimethicone, phenyl methicone, triphenyl trimethicone, bis diphenylethyl disiloxane, diphenylethyl benzyloxy disiloxane, isopentyl trimethoxycinnamate trisiloxane, phenyl ethyl disiloxane, benzylidene malonate polysiloxane, phenylpropyl ethyl methicone, and mixtures thereof.

3. The chromatic water-in-silicone emulsion of claim 2, wherein said phenylated silicone is selected from the group consisting of diphenyl dimethicone, phenyl trimethicone, phenylpropylethyl methicone, trimethyl pentaphenyl trisiloxane, tetramethyl tetraphenyl trisiloxane, phenylpropyl trimethicone, benzylidene malonate polysiloxane, and mixtures thereof.

4. The chromatic water-in-silicone emulsion of claim 1, wherein the aromatic silicone is present in an amount of from about 0.1 to about 10% by weight of the emulsion.

5. The chromatic water-in-silicone emulsion of claim 1, wherein the silicone fluid carrier is a volatile linear or volatile branched silicone fluid carrier having a viscosity of about 5 centistokes or less.

6. The chromatic water-in-silicone emulsion of claim 5, wherein the silicone fluid carrier is selected from the group consisting of dimethicone, trisiloxane, and mixtures thereof.

7. The chromatic water-in-silicone emulsion of claim 1, wherein the silicone fluid carrier is present in an amount of from about 0.01 to about 99% by weight of the emulsion.

8. The chromatic water-in-silicone emulsion of claim 7, wherein the silicone fluid carrier is present in an amount of from about 0.1 to about 50% by weight of the emulsion.

9. The chromatic water-in-silicone emulsion of claim 8, wherein the silicone fluid carrier is present in an amount of from about 0.5 to about 10% by weight of the emulsion.

10. The chromatic water-in-silicone emulsion of claim 1, wherein the silicone emulsifier is selected from the group consisting of ethoxylated silicones, propoxylated silicones, and mixtures thereof, said emulsifiers being with or without alkylation.

11. The chromatic water-in-silicone emulsion of claim 10, wherein the emulsifier comprises about 0.1 to about 50% by weight of the silicone phase.

12. The chromatic water-in-silicone emulsion of claim 11, wherein the emulsifier comprises about 1 to about 10% by weight of the silicone phase.

13. The chromatic water-in-silicone emulsion of claim 1, wherein the silicone emulsifier is selected from the group consisting of PEG/PPG-19/19 dimethicone, PEG/PPG-18/13 dimethicone, lauryl PEG/PPG-18/18 methicone, cetyl PEG/PPG-10/1 dimethicone, and mixtures thereof.

14. The chromatic water-in-silicone emulsion of claim 13, wherein the silicone emulsifier is PEG/PPG-19/19 dimethicone.

15. The chromatic water-in-silicone emulsion of claim 1, wherein the water-soluble polyol is selected from the group consisting of molecules with 3 or more carbon atoms, and 2 or more hydroxyl groups.

16. The chromatic water-in-silicone emulsion of claim 1, wherein the water-soluble polyol is present in an amount of from about 20 to about 50% by weight of the emulsion.

17. The chromatic water-in-silicone emulsion of claim 16, wherein the water-soluble polyol is present in an amount of from about 20 to about 40% by weight of the emulsion.

18. The chromatic water-in-silicone emulsion of claim 1, wherein the water-soluble polyol is selected from the group consisting of propylene glycol, methyl propane diol, butylene glycol, pentylene glycol, hexylene glycol, glycerin, sorbitol, dipropylene glycol, diglycerin, and mixtures thereof.

19. The chromatic water-in-silicone emulsion of claim 1, further comprising an alcohol present in the aqueous phase, the alcohol being selected from the group consisting of ethanol, isopropanol, and mixtures thereof.

20. The chromatic water-in-silicone emulsion of claim 19, wherein the alcohol is present in an amount of from about 10-30%, by weight of the aqueous phase.

21. The chromatic water-in-silicone emulsion of claim 1, wherein the water-soluble thickener is a polymer containing an acrylate monomer.

22. The chromatic water-in-silicone emulsion of claim 21, wherein the water-soluble polymer thickener is a carbomer having reduced impurities.

23. The chromatic water-in-silicone emulsion of claim 1, wherein the water-soluble polymer thickener is present in an amount from about 0.1 to about 5% by weight.

24. The chromatic water-in-silicone emulsion of claim 1 wherein the turbidity is less than about 10 NTU.

25. The chromatic water-in-silicone emulsion of claim 24, wherein the refractive index of the aqueous phase is within about 0.0001 of the refractive index of the silicone phase.

26. The chromatic water-in-silicone emulsion of claim 1, wherein said aqueous phase comprises from about 50 to 95% by weight of said emulsion.

27. The chromatic water-in-silicone emulsion of claim 26, wherein said aqueous phase comprises about 75 to 95% by weight said emulsion.

28. The chromatic water-in-silicone emulsion of claim 27, wherein said aqueous phase comprises droplets having a mean cross-sectional diameter of from about 20 to about 200 microns.

29. The chromatic water-in-silicone emulsion of claim 1, wherein said emulsion further comprises at least one member selected from the group consisting of colorants, fragrances, chelators, UV absorbers, sunscreens, silicone polymeric thickeners, vitamins, antioxidants, esters, emollients, anti-aging ingredients, pH adjusters, and mixtures thereof.

30. The chromatic water-in-silicone emulsion of claim 1, wherein said aqueous phase is substantially free of inorganic salt.

31. The chromatic water-in-silicone emulsion of claim 1, wherein said emulsion contains a fragrance.

32. A process for preparing a stable, chromatic water-in-silicone emulsion of claim 1 comprising:
(a) preparing an aqueous phase containing a water-soluble polyol, a water-soluble polymer thickener, and water;
(b) gelling or allowing the aqueous phase to gel;
(c) preparing a silicone phase containing an aromatic silicone, a silicone emulsifier and silicone fluid carrier; and (d) combining the aqueous and silicone phases under sufficient conditions whereby the gel inverts to form a water-in-silicone emulsion with a silicone phase and an aqueous internal phase.

33. A stable, chromatic water-in-silicone emulsion comprising:
   i) from about 1 to about 95% of an aqueous phase, the aqueous phase containing from about 20 to about 90% of one or more water-soluble polyols, from about 0.1 to about 5% of a water-soluble polymer thickener, and water; and
   ii) a silicone phase containing from about 0.1 to about 10% of a phenylated aromatic silicone, a silicone emulsifier, and from about 0.1 to about 50% of a silicone fluid carrier, the silicone emulsifier being present in the emulsion in an amount of from about 1 to about 10% by weight of the silicone phase, all concentrations except as otherwise indicated being by weight based on the total weight of the emulsion, wherein the refractive index of the aqueous phase is within about 0.0004 of the refractive index of the silicone phase, and wherein the refractive indices of the two phases are sufficiently matched to produce a turbidity of less than or equal to about 100 NTU at 25° C.

* * * * *